United States Patent [19]

Bucalo

[11] 4,024,855

[45] May 24, 1977

[54] MAGNETIC FILAMENTARY STRUCTURE AND METHOD FOR USING THE SAME

[76] Inventor: Louis Bucalo, 155 Roberts St., Holbrook, N.Y. 11741

[22] Filed: Nov. 18, 1975

[21] Appl. No.: 633,015

Related U.S. Application Data

[62] Division of Ser. No. 537,572, Dec. 30, 1974, Pat. No. 3,982,537.

[52] U.S. Cl. .............................. 128/1 R; 128/1.3; 128/130; 128/DIG. 25
[51] Int. Cl.² ....................................... A61B 19/00
[58] Field of Search .................. 128/1 R, 1.3–1.5, 128/130, 335.5, 419 F, DIG. 25

[56] References Cited

UNITED STATES PATENTS

| 255,292 | 3/1882 | Hussey et al. | 128/1.3 |
| 3,710,399 | 1/1973 | Hurst | 128/1.3 |
| 3,794,041 | 2/1974 | Frei et al. | 128/1.3 |
| 3,815,578 | 6/1974 | Bucalo | 128/1 R |
| 3,924,631 | 12/1975 | Mancusi, Jr. | 128/DIG. 25 |
| 3,939,821 | 2/1976 | Roth | 128/1 R |

OTHER PUBLICATIONS

Driller, "IEEE Transactions on Magnetics", vol. mag. 9, No. 3, Sept., 1973, pp. 444–447.

Primary Examiner—William E. Kamm
Attorney, Agent, or Firm—Steinberg & Blake

[57] ABSTRACT

A magnetic structure in the form of a filament which can be wound into a coil or the like. Such a structure can be made compatible with human tissue and implanted so that with a pair of such coils, for example, situated on opposite sides of a passage such as the urethra, it is possible to control the flow of fluid through a body passage.

9 Claims, 5 Drawing Figures

MAGNETIC FILAMENTARY STRUCTURE AND METHOD FOR USING THE SAME

CROSS REFERENCE TO RELATED APPLICATION

This application is a division of copending application Ser. No. 537,572, filed Dec. 30, 1974 now U.S. Pat. No. 3,982,537.

BACKGROUND OF THE INVENTION

The present invention relates to magnetic structures and methods for using magnetic structures, particularly in living beings.

It has already been proposed to provide magnetic structures suitable for implantation in a living being such as a human being. For example, in connection with problems of incontinence, it has been proposed to use magnetic structures which on the one hand are capable of holding a body passage such as the urethra closed and which are capable of being acted upon by a magnet exterior to the body for opening the body passage.

However, devices of this type suffer from several drawbacks. Thus, devices of this type in general are capable of pinching the tube through which the body fluid flows in order to shut the tube and then releasing the tube so that the fluid can flow therethrough. However, such devices have a serious disadvantage in that necrosis is unavoidable. Thus, with devices of this type pressure is applied against the tissue from solid bodies in such a way that nourishment cannot reach the tissue which is under pressure, and necrosis of such tissue is unavoidable.

SUMMARY OF THE INVENTION

It is accordingly a primary object of the present invention to provide a method and structure which will avoid the above drawbacks.

Thus, it is an object of the present invention to provide a flexible filament which has magnetic properties and which is not only of general utility but also of particular utility in connection with body implants.

In particular it is an object of the present invention to provide a structure capable of being used in an effective manner for controlling the flow of a fluid through a body passage while avoiding the possibility of necrosis.

According to the method of the invention there is implanted in body tissue a filamentary permanent magnet having a configuration which will enable ingrowth of tissue to take place next to and along the filamentary magnet so that the magnetic properties thereof are capable of giving to the tissue in which it is implanted a muscular characteristic. The structure of the invention includes a filament which may be of general utility and which has the properties of a permanent magnet.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
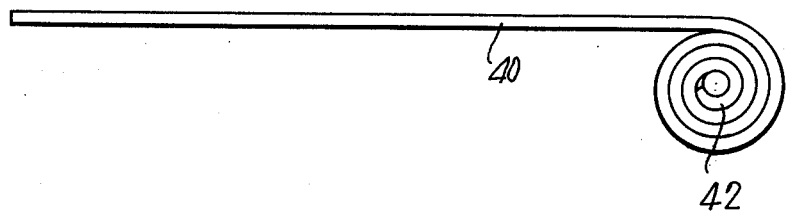
FIG. 1 illustrates a filamentary magnetic structure of the invention.
Figure 2:
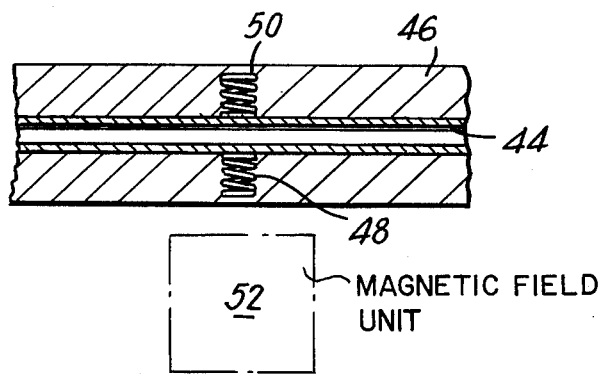
FIG. 2 illustrates how the structure of FIG. 1 may be used in an implant for controlling flow of body fluid.

In accordance with the invention, an implant of the type shown in FIGS. 1 and 2 is provided. Thus, referring to FIG. 1, there is shown therein an elongated metallic filament 40 which is made of a permanent magnet material. For example this filament 40 may be made of a platinum-cobalt alloy. As is well known such an alloy forms an excellent permanent magnet while at the same time being compatible with tissue of a subject such as a human being. This filamentary permanent magnet 40 is obtained from such an alloy be being drawn into the fine wire-like form shown in FIG. 1, and in this filamentary form the magnet material 40 may be wound on a suitable small spool 42 so as to have the configuration of a coil.

The invention, however, is not limited to an alloy such as a platinum-cobalt alloy. For example it is possible to provide a filament having the same mechanical properties as the filament 40 but composed of gold, for example, which is compatible with tissue of the body and which has embedded therein particles of Alnico or the like, which also form excellent permanent magnets. These permanent magnet particles are distributed throughout such a gold filament which forms a fine wire which also may be wound onto a small spool 42 as shown in FIG. 1.

The manner in which the structure of FIG. 1 is used is illustrated in FIG. 2. Thus FIG. 2 schematically illustrates a body tube such as a urethra 44 which is surrounded by tissue 46. A small coil 48 in the form of a permanent magnet element is embedded in the tissue 46 in the manner shown in FIG. 2 so that this filamentary permanent magnet becomes situated close to the tube 44 on one side thereof. On the opposite side of the tube 44 there is implanted a second fine filamentary coil 50 which can either be a second permanent magnet filament or simply a filament which has magnetic properties but is not a permanent magnet. For example a fine gold wire may have embedded therein and dispersed therethrough tiny particles of iron which have the required magnetic properties while not necessarily forming a permanent magnet.

With such filamentary implants 48 and 50 situated as shown in FIG. 2, it is possible to give to the implants a polarity which will cause them to attract each other for the purpose of pinching the tube 44 closed. Such an implant is of particular utility with individuals who suffer from incontinence. Where such an individual cannot control the flow of fluid through the tube 44, the implant of the invention will enable the tube 44 to be maintained closed. In order to open the tube, it is only necessary to situate adjacent the body of the individual, in the region of the implant 48 and 50 a unit such as the unit 52 shown in phantom lines in FIG. 2. This unit will create a magnetic field which will alter the polarity of the implants 48 and 50 so that they will repel each other to open the tube 44, permitting the body fluid to discharge, and thereafter the unit 42 may return the implants 48 and 50 to their original polarity where they will attract each other and again close the body 44.

One of the great advantages which is achieved with an arrangement as shown in FIG. 2 is that the filamentary implants 48, 50 provide for free growth of tissue into all spaces between the adjoining portions of the filamentary structure so that tissue ingrowth takes place for surrounding the filaments with the tissue in such a way that when the tube 44 is pinched, for example, necrosis will not occur as would be the case if solid plates or the like were used. Moreover, the filamentary structures may have certain springy characteristics which in addition to the magnetic characteristics provide the equivalent of a muscular structure.

As was pointed out above, the filamentary implant 48 may be permanent magnet while the filamentary implant 50 may either be a permanent magnet or simply a filament having magnetic properties. In either case it is possible through a unit such as the unit 52 to control the attraction or repulsion of the units 48 and 50 for the purpose of closing or opening the tube 44.

Figure 3:
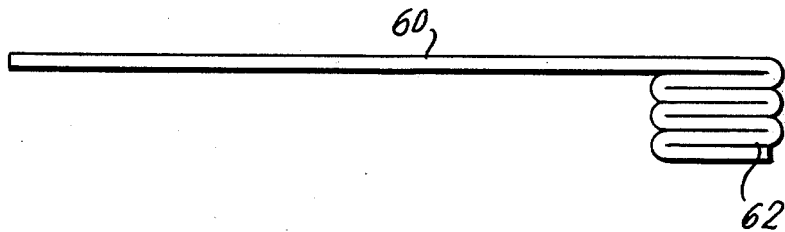
FIG. 3 shows another embodiment of a filamentary magnetic structure of the invention.

In connection with FIGS. 1 and 2, it is to be noted that it is not essential to wind or shape the filament 40 into a coil form. Thus, as is shown in FIG. 3, a filament 60 which is in all respects identical with the filament 40, may be fed back and forth by any suitable structure so as to be shaped into a pad 62, which may be similar to a small steel wool pad in its construction, and this pad 62 can be used in the same say as the coil type of implants.

What is claimed is:

1. In a method to be performed on subjects such as human beings, animals, and the like, the step of implanting in internal tissue of the subject a means for dynamically acting through the tissue in which it is implanted for changing the condition of the subject, said means which is implanted in said tissue including a filamentary permanent magnet structure shaped to have a configuration providing between adjoining portions of the filamentary structure spaces which will enable ingrowth of tissue to take place into said spaces of the filamentary magnet so that the magnetic properties thereof are capable of giving to the tissue in which it is implanted a muscular characteristic.

2. In a method as recited in claim 1 and wherein said filamentary magnet is implanted on one side of a tube through which a fluid is adapted to flow, and said means including a magnetic filamentary structure situated on the other side of said tube, so that through magnetic attraction of said filamentary magnetic structure and said filamentary permanent magnet it is possible to exert pressure on said tube closing the latter while minimizing necrosis.

3. In a method as recited in claim 2 and including the step of providing at the exterior of the subject in the regions of said filamentary magnet and filamentary magnetic structure a field which will act to create a repulsive force between the filamentary magnet and the filamentary magnetic structure for opening said tube when desired.

4. In a method as recited in claim 2 and wherein said filamentary magnetic structure is a second filamentary permanent magnet.

5. In a method as recited in claim 2 and wherein said filamentary magnetic structure is capable of being magnetically acted upon but is not itself a permanent magnet.

6. A body made up of a filamentary structure having the properties of a permanent magnet and including filamentary portions situated next to and adjoining each other and defining between themselves spaces into which tissue can grow when the body is implanted.

7. A body as recited in claim 6, said filamentary structure being made of a metal such as a platinum-cobalt alloy.

8. A body as recited in claim 6 and wherein the material of the filamentary structure is compatible with tissue of tissue of the human body.

9. A body as recited in claim 8 and wherein the filamentary structure consists of filamentary material, such as gold, which is compatible with the tissue of the human body, and said material having embedded therein and dispersed therethrough permanent magnetic particles.

* * * * *